United States Patent
Yoshimoto et al.

(10) Patent No.: US 10,053,419 B2
(45) Date of Patent: Aug. 21, 2018

(54) ISOCYANATE COMPOUND MANUFACTURING METHOD

(71) Applicant: SUMITOMO CHEMICAL COMPANY, LIMITED, Tokyo (JP)

(72) Inventors: Yuya Yoshimoto, Takarazuka (JP); Masaji Hirota, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/531,637

(22) PCT Filed: Nov. 27, 2015

(86) PCT No.: PCT/JP2015/083356
§ 371 (c)(1),
(2) Date: May 30, 2017

(87) PCT Pub. No.: WO2016/098561
PCT Pub. Date: Jun. 23, 2016

(65) Prior Publication Data
US 2017/0342023 A1     Nov. 30, 2017

(30) Foreign Application Priority Data

Dec. 17, 2014  (JP) .................................. 2014-254824
Jan. 8, 2015   (JP) .................................. 2015-002061

(51) Int. Cl.
*C07C 263/10*     (2006.01)

(52) U.S. Cl.
CPC .................................. *C07C 263/10* (2013.01)

(58) Field of Classification Search
CPC .......................... C07C 263/10; C07C 265/12
See application file for complete search history.

(56) References Cited

U.S. PATENT DOCUMENTS

| 5,925,783 | A | * | 7/1999 | Jost ........................ C07C 263/10 560/347 |
| 6,060,484 | A | | 5/2000 | Fritz et al. |
| 2016/0081339 | A1 | | 3/2016 | Yoshimoto et al. |

FOREIGN PATENT DOCUMENTS

| CN | 1687022 A | 10/2005 |
| CN | 1939899 A | 4/2007 |
| JP | 2000-510833 A | 8/2000 |
| JP | 2014-80415 A | 5/2014 |
| WO | WO 2013/162072 A1 | 10/2013 |
| WO | WO 2014/175465 A1 | 10/2014 |

OTHER PUBLICATIONS

International Preliminary Report on Patentability and English translation of the Written Opinion of the International Searching Authority (Forms PCT/IB/373 and PCT/ISA/237), dated Jun. 20, 2017, for International Application No. PCT/JP2015/083356.
International Search Report, issued in PCT/JP2015/083356, dated Jan. 19, 2016.
Chinese First Office Action (including an English translation thereof) issued in the corresponding Chinese Patent Application No. 201580067677.X dated Jan. 8, 2018.
Wang et al., Synthesis of substituted phenyl isocyanates by bis(trichloromethyl) carbonate method, Applied Chemical Industry, vol. 37, No. 9, Sep. 2008, pp. 1019-1021.

* cited by examiner

*Primary Examiner* — Pancham Bakshi
*Assistant Examiner* — Mark R Luderer
(74) *Attorney, Agent, or Firm* — Birch, Stewart, Kolasch & Birch, LLP

(57) ABSTRACT

By reacting 3-methyl-2-methoxymethylaniline, etc. with a phosgene compound in the presence of a tertiary amine at 10° C. to 14° C. in at least one kind of solvent selected from a group consisting of chlorobenzene and ortho-dichlorobenzene, an isocyanate compound such as 3-methyl-2-methoxymethyl-1-isocyanatobenzene can be manufactured with good yields.

5 Claims, No Drawings

ISOCYANATE COMPOUND MANUFACTURING METHOD

TECHNICAL FIELD

The present invention relates to a method for manufacturing an isocyanate compound.

BACKGROUND ART

A compound represented by formula (2)

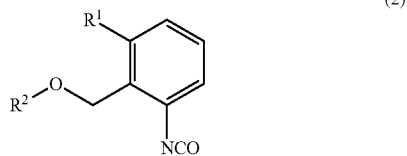

(2)

[wherein $R^1$ represents a methyl group, a cyclopropyl group, a chlorine atom, a bromine atom, an ethyl group or a methoxy group; and $R^2$ represents an alkyl group having 1 to 6 carbon atoms] (hereinafter, referred to as "compound (2)") is useful as an intermediate for an agrochemical (see WO 2013/162072), and can be manufactured by reacting a compound represented by formula (1)

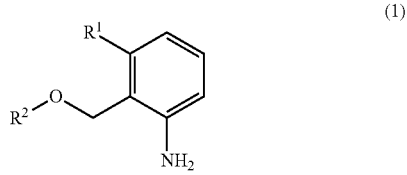

(1)

[wherein $R^1$ and $R^2$ are as defined above] (hereinafter, referred to as "compound (1)"), which is an aniline compound corresponding to compound (2), with a phosgene compound. More specifically, 3-methyl-2-methoxymethyl-1-isocyanatobenzene can be manufactured by stirring 3-methyl-2-methoxymethyl-1-aminobenzene, triphosgene, saturated aqueous sodium bicarbonate and ethyl acetate together under ice-cooling, as described in Reference Production Example 18 in WO 2013/162072.

SUMMARY OF THE INVENTION

However, the method disclosed in WO 2013/162072 is not a satisfactory industrial-scale manufacturing method with respect to yield. The present invention provides a method for manufacturing an isocyanate compound such as 3-methyl-2-methoxymethyl-1-isocyanatobenzene with higher yield.

According to the present invention, compound (2) can be manufactured by reacting compound (1) with a phosgene compound at 10° C. to 14° C. in the presence of a tertiary amine in at least one kind of solvent selected from the group consisting of chlorobenzene and ortho-dichlorobenzene.

MODE FOR CARRYING OUT THE INVENTION

Specific examples of the alkyl group having 1 to 6 carbon atoms mentioned as $R^2$ include a methyl group, an ethyl group, a propyl group, an isopropyl group, a butyl group, a sec-butyl group, a tert-butyl group, a pentyl group and a hexyl group. The alkyl group is preferably a methyl group or an ethyl group.

Compound (2) can be manufactured by reacting compound (1) with a phosgene compound at 10° C. to 14° C. in the presence of a tertiary amine in at least one kind of solvent selected from the group consisting of chlorobenzene and ortho-dichlorobenzene.

The solvent to be used in the reaction is chlorobenzene, ortho-dichlorobenzene or a mixture thereof, and is preferably chlorobenzene. The amount of the solvent to be used is generally 3 to 20 times the weight of compound (1).

The phosgene compound to be used in the reaction is phosgene, diphosgene (trichloromethyl chloroformate) or triphosgene (bis(trichloromethyl) carbonate), and is preferably triphosgene.

Diphosgene and triphosgene are decomposed in reaction systems to be converted to two equivalents of phosgene and three equivalents of phosgene, respectively. The amount of the phosgene compound to be used is generally 0.95 to 1.5 equivalents, preferably 1.0 to 1.3 equivalents, relative to 1 equivalent of compound (1).

Specific examples of the tertiary amine to be used in the reaction include triethylamine, diisopropylethylamine, N-methylmorpholine, N-methylpiperidine and 1,8-diazabicyclo[5.4.0]undec-7-ene. The tertiary amine is preferably a trialkylamine such as triethylamine and diisopropylethylamine, and is more preferably triethylamine. The amount of the tertiary amine to be used is generally 1.8 to 2.5 equivalents, preferably 2.0 to 2.2 equivalents, relative to 1 equivalent of the phosgene compound.

The reaction temperature is 10° C. to 14° C., as mentioned above.

The order of mixing of compound (1), the phosgene compound and the tertiary amine is preferably as follows: compound (1) is added to the solvent and the phosgene compound, and then the tertiary amine is added to the resultant mixture. From the viewpoint of the yield, it is preferred to add dropwise each of the compounds in portions. The time of the dropwise addition of each of the compounds is generally 30 minutes to 24 hours. It is preferred that compound (1) be added dropwise over 2 to 24 hours and the tertiary amine be added dropwise over 4 to 24 hours.

After the completion of the dropwise addition of each of the compounds, the solution is generally stirred at 10° C. to 14° C. for 0.1 to 6 hours.

After the completion of the reaction, compound (2) can be isolated by carrying out a post-treatment procedure, such as filtration, of the reaction mixture. The compound (2) may be purified by a procedure such as distillation and chromatography.

EXAMPLES

Example 1

Triphosgene (31.4 g) was dissolved in chlorobenzene (200 g) under a nitrogen atmosphere, and then the resultant solution was cooled to 12° C. 3-Methyl-2-methoxymethyl-aniline (40.0 g) was added to the solution dropwise over 3 hours at the same temperature. After the completion of the dropwise addition, the solution was further stirred for 1.5 hours at the same temperature. A mixture of triethylamine (64.2 g) and chlorobenzene (40 g) was dropwise added to the resultant mixture over 5 hours, and the resultant solution was further stirred for 3 hours to cause the precipitation of crystals. The crystals were filtered, and a filtrate was analyzed by liquid chromatography. As a result, it was found that 3-methyl-2-methoxymethyl-1-isocyanatobenzene (45.7 g) was contained in the filtrate (yield: 97.4%).

Example 2

Triphosgene (31.4 g) was dissolved in chlorobenzene (200 g) under a nitrogen atmosphere, and then the resultant solution was cooled to 10° C. 3-Methyl-2-methoxymethylaniline (40.0 g) was added to the solution dropwise over 3 hours at the same temperature. After the completion of the dropwise addition, the solution was further stirred for 1.5 hours at the same temperature. A mixture of triethylamine (64.2 g) and chlorobenzene (40 g) was added to the resultant mixture dropwise over 5 hours, and the resultant solution was further stirred for 3 hours to cause the precipitation of crystals. The crystals were filtered, and a filtrate was analyzed by liquid chromatography. As a result, it was found that 3-methyl-2-methoxymethyl-1-isocyanatobenzene (44.6 g) was contained in the filtrate (yield: 95.0%).

Example 3

Triphosgene (31.4 g) was dissolved in chlorobenzene (200 g) under a nitrogen atmosphere, and then the resultant solution was cooled to 14° C. 3-Methyl-2-methoxymethylaniline (40.0 g) was added to the solution dropwise over 3 hours at the same temperature. After the completion of the dropwise addition, the solution was further stirred for 1.5 hours at the same temperature. A mixture of triethylamine (64.2 g) and chlorobenzene (40 g) was added to the resultant mixture dropwise over 5 hours, and the resultant solution was further stirred for 3 hours to cause the precipitation of crystals. The crystals were filtered, and a filtrate was analyzed by liquid chromatography. As a result, it was found that 3-methyl-2-methoxymethyl-1-isocyanatobenzene (45.0 g) was contained in the filtrate (yield: 95.9%).

Reference Examples

Triphosgene (31.4 g) was dissolved in chlorobenzene (200 g) under a nitrogen atmosphere, and then 3-methyl-2-methoxymethylaniline (40.0 g) was added to the solution dropwise at each of the temperatures shown in the table below over 2 to 3 hours. After the completion of the dropwise addition, the solution was further stirred for 2 hours at the same temperature. A mixture of triethylamine (64.2 g) and chlorobenzene (40 g) was added to the resultant mixture dropwise over 4 to 6 hours, and the resultant solution was further stirred for 3 hours to cause the precipitation of crystals. The crystals were filtered, and a filtrate was analyzed by liquid chromatography. As a result, it was found that 3-methyl-2-methoxymethyl-1-isocyanatobenzene was manufactured with each of the yields shown in Table 1.

TABLE 1

|  | Reference Example 1 | Reference Example 2 | Reference Example 3 | Reference Example 4 |
|---|---|---|---|---|
| Reaction temperature | 0-3° C. | 5-8° C. | 25-28° C. | 15-17° C. |
| Yield | 66.6% | 89.4% | 26.8% | 85.9% |

Example 4

Chlorobenzene (254.64 g) was cooled to 12° C. under a nitrogen atmosphere. The dropwise addition of 3-methyl-2-methoxymethylaniline (52.44 g) and the bubbling with a phosgene gas (46.31 g) were carried out simultaneously over 3 hours at the same temperature. After the completion of the dropwise addition and the bubbling, the resultant solution was further stirred at the same temperature for 1.5 hours. A mixture of triethylamine (94.75 g) and chlorobenzene (52.44 g) was added to the resultant mixture dropwise over 5 hours, and the resultant solution was further stirred for 3 hours to cause the precipitation of crystals. The crystals were filtered, and a filtrate was analyzed by liquid chromatography. As a result, it was found that 3-methyl-2-methoxymethyl-1-isocyanatobenzene (57.9 g) was contained in the filtrate (yield: 94.2%).

INDUSTRIAL APPLICABILITY

According to the present invention, it becomes possible to manufacture an isocyanate compound with industrially satisfactory yield.

The invention claimed is:

1. A method for manufacturing an isocyanate compound of formula (2)

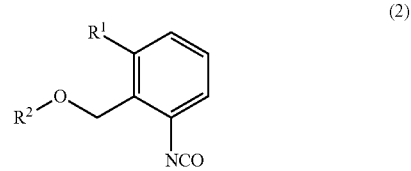

(2)

wherein $R^1$ is a methyl group, a cyclopropyl group, a chlorine atom, a bromine atom, an ethyl group or a methoxy group; and $R^2$ is an alkyl group having 1 to 6 carbon atoms, comprising reacting a compound of formula (1)

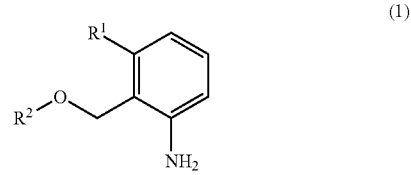

(1)

wherein $R^1$ and $R^2$ are as defined above, with a phosgene compound at 10° C. to 14° C. in the presence of a tertiary amine in at least one kind of solvent selected from the group consisting of chlorobenzene and ortho-dichlorobenzene.

2. The manufacturing method according to claim 1, wherein $R^1$ is a methyl group and $R^2$ is a methyl group.

3. The manufacturing method according to claim 1, wherein the phosgene compound is triphosgene.

4. The manufacturing method according to claim 1, wherein the tertiary amine is triethylamine.

5. The manufacturing method according to claim 1, wherein the solvent is chlorobenzene.

* * * * *